(12) United States Patent
Shetty

(10) Patent No.: US 10,576,117 B2
(45) Date of Patent: Mar. 3, 2020

(54) HERBO-MINERAL FORMULATION FOR PREVENTION, TREATMENT AND MANAGEMENT OF DIABETES AND METHOD OF PREPARATION THEREOF

(71) Applicant: Muniyal Ayurvedic Research Centre, Manipal (IN)

(72) Inventor: M Vijayabhanu Shetty, Manipal (IN)

(73) Assignee: Muniyal Ayurvedic Research Centre, Manipal (IN)

( * ) Notice: Subject to any disclaimer, the term of this patent is extended or adjusted under 35 U.S.C. 154(b) by 0 days.

(21) Appl. No.: 16/232,573

(22) Filed: Dec. 26, 2018

(65) Prior Publication Data

US 2019/0125816 A1 May 2, 2019

Related U.S. Application Data

(63) Continuation of application No. 15/960,343, filed on Apr. 23, 2018.

(60) Provisional application No. 62/489,142, filed on Apr. 24, 2017.

(51) Int. Cl.

| | | |
|---|---|---|
| *A61K 36/00* | (2006.01) | |
| *A61K 36/25* | (2006.01) | |
| *A61K 36/185* | (2006.01) | |
| *A61K 36/9066* | (2006.01) | |
| *A61K 36/37* | (2006.01) | |
| *A61K 36/24* | (2006.01) | |
| *A61K 36/61* | (2006.01) | |
| *A61K 36/59* | (2006.01) | |
| *A61K 45/06* | (2006.01) | |
| *A61P 3/10* | (2006.01) | |
| *A61K 36/328* | (2006.01) | |
| *A61K 36/9068* | (2006.01) | |
| *A61K 36/67* | (2006.01) | |
| *A61K 33/30* | (2006.01) | |
| *A61K 35/614* | (2015.01) | |

(52) U.S. Cl.
CPC ............. *A61K 36/37* (2013.01); *A61K 33/30* (2013.01); *A61K 35/614* (2013.01); *A61K 36/185* (2013.01); *A61K 36/24* (2013.01); *A61K 36/328* (2013.01); *A61K 36/59* (2013.01); *A61K 36/61* (2013.01); *A61K 36/67* (2013.01); *A61K 36/9066* (2013.01); *A61K 36/9068* (2013.01); *A61K 45/06* (2013.01); *A61P 3/10* (2018.01); *A61K 2300/00* (2013.01)

(58) Field of Classification Search
CPC .. A61K 36/00; A61K 36/424; A61K 36/9066; A61K 36/185; A61K 36/25
USPC ................ 424/756, 779, 773, 748, 777, 728
See application file for complete search history.

(56) References Cited

U.S. PATENT DOCUMENTS

| | | | | |
|---|---|---|---|---|
| 2006/0019907 A1* | 1/2006 | Aggarwal | ............. | A61K 31/56 514/26 |
| 2009/0214678 A1* | 8/2009 | Dubey | .................. | A61K 36/42 424/725 |

FOREIGN PATENT DOCUMENTS

| | | | | |
|---|---|---|---|---|
| IN | 1813/CHE/2005 | * | 3/2006 | ............. A61K 36/00 |
| IN | 2012/MUM/01755 | * | 3/2013 | ............. A61K 36/00 |
| WO | WO-2010057503 A2 | * | 5/2010 | ........... A61K 31/655 |

* cited by examiner

*Primary Examiner* — Michael Barker
*Assistant Examiner* — Deborah A Davis
(74) *Attorney, Agent, or Firm* — Pilloff & Passino LLP; Sean A. Passino; Rachel K. Pilloff

(57) ABSTRACT

Herbo-mineral formulation for prevention, treatment and management of Diabetes and method of preparing the same are disclosed herein. The disclosed herbo-mineral formulation includes herb and mineral elements which facilitate in treating Diabetes and Diabetes associated complications. Further the disclosed formulation has been observed to exhibit hypoglycemic, hypolipidemic, and pancreatic cell regenerative properties.

12 Claims, 12 Drawing Sheets

HERBO-MINERAL FORMULATION FOR PREVENTION, TREATMENT AND MANAGEMENT OF DIABETES AND METHOD OF PREPARATION THEREOF

CROSS REFERENCE TO RELATED APPLICATION

This application is a continuation of the U.S. application Ser. No. 15/960,343 filed on Apr. 23, 2018, which in turn claims priority of the U.S. provisional application 62/489,142 filed on Apr. 24, 2017, the contents of which are incorporated herein by reference

TECHNICAL FIELD

The embodiments disclosed in this specification relates to herbo-mineral formulation effective in the treatment, management and prevention of Diabetes, in particular Diabetes mellitus and related complications. It also relates to the process of preparation of such formulation.

BACKGROUND

Diabetes is a condition, an epidemic, associated with increased blood sugar level (hyperglycemia). The condition is a result of impaired glucose uptake by cells. Glucose uptake by cells from the blood stream is facilitated by Insulin. Inadequate insulin production by pancreas or inability of the body to use the produced insulin causes Diabetes.

While, family history is considered as one of the risk factors in developing Diabetes, lifestyle and environmental factors also play a role in increasing the risk. Lifestyle factors including lack of physical activity, obesity, poor diet, cigarette smoking, etc. increase the risk of developing Diabetes.

Diabetes is considered as a condition that lasts a lifetime and that can only be controlled but may never be cured. The disease when uncontrolled could lead to various life threatening complications such as glaucoma, neuropathy, atherosclerosis, kidney failure, hypertension, depression, anxiety, gastroparesis, stroke, diabetic hyperlipidemia, etc.

Diabetes not just affects the quality of life of an individual on a day to day basis but also increases the risks of severity and complications in case of any health incident. In any case, managing/handling diabetic patient is a complicated and expensive affair considering the nature of special care that may have to be implemented.

Existing treatment methods include hypoglycemic drugs, Insulin injections, and so on. However, such allopathic interventions have been known to have side effects such as nausea, vomiting, drowsiness, numbness, muscle pain, etc.

Alternatively, ayurvedic treatment methods have also been developed to treat Diabetes. Ancient teaching of Ayurveda disclose the use of herbs such as *Glycerrhiza glabra, Terminalia bellirica, Phyllanthus emblica, Terminalia arjuna, Santalum alba, Terminalia chebula* and *Curcuma Longa* in treatment of Diabetes. Many other formulations including herbs such as *Berberis aristata, Rubi cordifolia, Trigonella foenum graecum, Azhadirachta indica, Curcuma Longa* and *Tinospora Cordifolia* have also been developed. It has been observed that about half of the patients with Type II diabetes mellitus can be managed with diet and exercise, and when Ayurvedic treatment is followed dose of insulin can be reduced even in Type I insulin dependent diabetes mellitus. While Ayurvedic treatment has many benefits, the effectiveness of most Ayurvedic herbal formulations is arguable. There exists a need for an effective method of treating/managing Diabetes.

OBJECTS OF THE DISCLOSED EMBODIMENTS

The principal object of the embodiments disclosed herein is to provide a composition and method of treating Diabetes and Diabetes associated complications.

A second object of the embodiments disclosed herein is to provide a composition and method of managing Diabetes and Diabetes associated complications.

Another object of the embodiments disclosed herein is to provide a composition and method of preventing Diabetes and Diabetes associated complications.

Another object of the embodiments disclosed herein is to provide a herbo-mineral formulation and a method for its preparation.

These and other objects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF FIGURES

The embodiments disclosed herein are illustrated in the accompanying drawings, throughout which like reference letters indicate corresponding parts in the various figures. The embodiments herein will be better understood from the following description with reference to the drawings, in which.

DETAILED DESCRIPTION

Figure 1A:
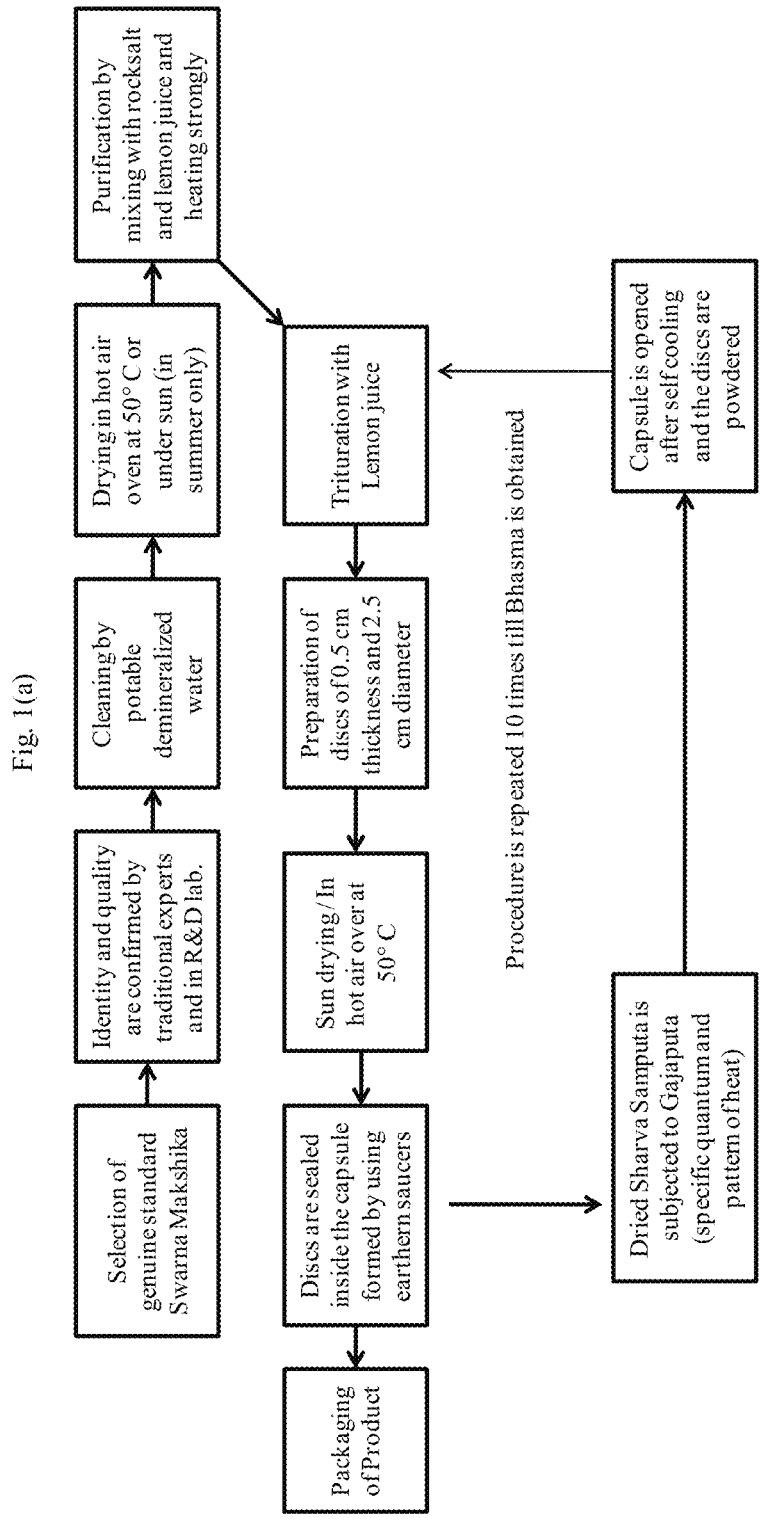
FIG. 1(a) depicts a flowchart for the preparation of Swarna Makshika Bhasma.
Figure 1B:
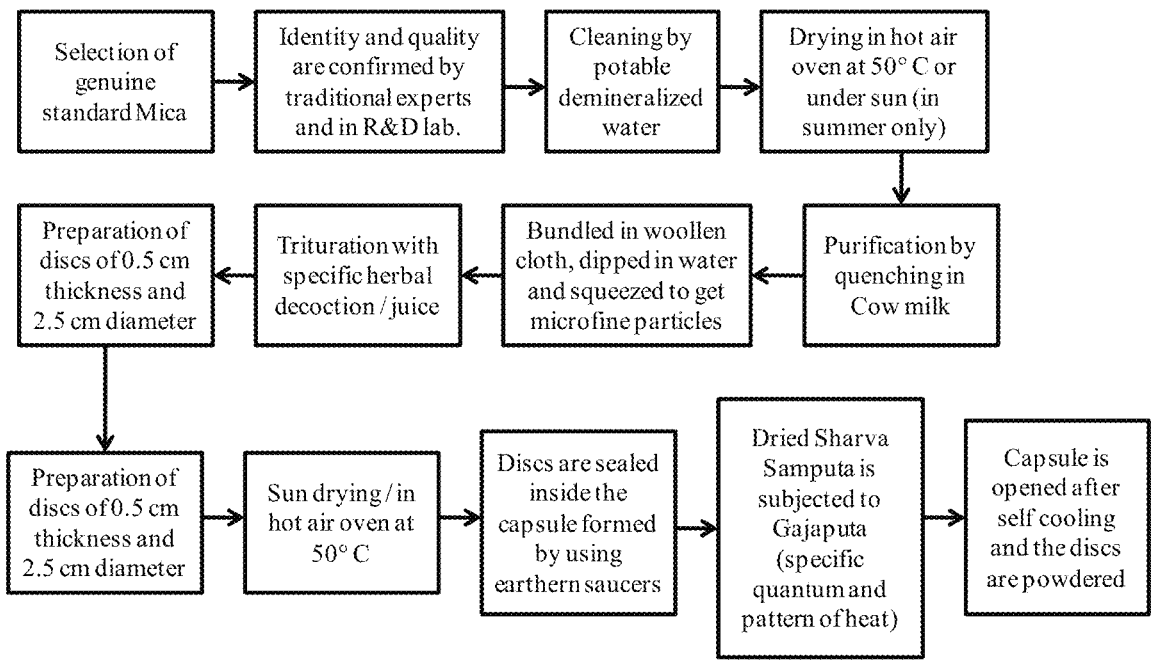
FIG. 1(b) depicts a flowchart for the preparation of Abhraka Bhasma.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein achieve a herbo-mineral formulation of therapeutic value, and a process for the preparation of the formulation. The herbo-mineral formulation disclosed herein is useful in the treatment, prevention and management of Diabetes and related metabolic disorders. The formulation, disclosed in the various embodiments herein, may also be used to treat hyperglycemia, hyperlipidemia, and other complications associated with Diabetes. It has also been observed that the embodiments of the disclosed formulation may be instrumental in preventing the complications of diabetes like retinopathy, neuropathy, nephropathy and vascular diseases. The herbo-mineral formulation, further, has been observed to have hypoglycemic, hypolipidemic, cytoprotective and immunomodulatory activities. The formulation may be used as monotherapy or as an adjunct with other oral hypoglycemic drugs.

Further, disclosed herein is a method of regenerating beta cells (β cells) and increasing cell mass in pancreas. The embodiments disclosed herein have surprisingly been observed to stimulate regeneration of β cells of islets of pancreas of diabetic rats. Accordingly, the embodiments disclosed herein achieve a method for the treating/managing Diabetes.

Formulation

The disclosed embodiments herein provide herbo-mineral formulation having a combination of selected herbs and minerals. In an embodiment, the herbo-mineral formulation includes herb element and mineral element. In another embodiment, the herbo-mineral formulation includes herb element, mineral element along with suitable excipient.

Herb Element

In an embodiment, the herb element includes the herbs *Salacia chinensis, Gymnema sylvestre, Emblica officinalis, Eugenia jambolana, Curcuma longa, Commiphora mukul* (Guggulu) and *Tinospora cordifolia* or their extracts, or the active ingredients extracted from these herbs. In another embodiment, the herb element further includes at least one of the herbs selected from *Withania somnifera, Terminalia chebula, Terminalia bellerica, Andrographis paniculata, Boerhavia diffusa, Azhadirachta indica, Aristolochia indica, Aegle marmelos, Cyperus rotundus, Hemedesmus indicus, Trichosanthes dioica, Santalum alba, Terminalia arjuna, Woodfordia fruiticosa, Glycerrhiza glabra, Mucuna pruriens, Myrica nagi, Plumbago rosea, Inula racemosa, Zingiber officinalis, Piper longum* and *Piper nigrum* or their extracts, or the active ingredients extracted from these herbs.

The herb element may be a specific part of the herb (also referred as herb component) such as roots, flowers, fruits, stem, bark, resin, rhizome, whole plant, etc. In an embodiment, the herb element may include roots of *Salacia chinensis, Withania somnifera, Boerhavia diffusa, Aristolochia indica, Aegle marmelos, Cyperus rotundus, Hemedesmus indicus, Glycerrhiza glabra* and *Plumbago rosea*; fruits of *Terminalia chebula, Terminalia bellerica, Emblica officinalis, Piper longum* and *Piper nigrum*; bark of *Azhadirachta indica, Myrica nagi* and *Terminalia arjuna*; plant of *Andrographis paniculata* and *Trichosanthes dioica*; leaves of *Gymnema sylvestre*; heartwood of *Santalum alba*; flowers of *Woodfordia fruiticosa*; seeds of *Mucuna pruriens* and *Eugenia jambolana*; rhizome of *Curcuma longa* and *Zingiber officinalis*; gum resin of *Commiphora mukul*, and stem of *Tinospora cordifolia* or their extract. However, it is also within the scope of the claims provided herein for the herbo-mineral formulation to include other herb components such as leaf, flowers, etc. without otherwise deterring intended function of the herbo-mineral formulation.

The herb component maybe included in the formulation in any form that is generally known in the field. For example, the herb component may be dried, powdered, processed to form concentrates, extracts, etc. In one preferred embodiment, the herb components are dried and powdered which is further incorporated into the formulation.

In an embodiment, the herb element includes *Salacia chinensis* in the range of 4 to 8 wt %, *Gymnema sylvestre* in the range of 4 to 8 wt %, *Emblica officinalis* in the range of 2 to 6 wt %, *Eugenia jambolana* in the range of 4 to 8 wt %, *Curcuma longa* in the range of 3 to 7 wt %, *Commiphora mukul* (Guggulu) in the range of 3 to 7 wt % and *Tinospora cordifolia* in the range of 3 to 7 wt %, of the total weight of the composition. Further, in another embodiment, the herb element includes at least one of *Withania somnifera, Terminalia chebula, Terminalia bellerica, Andrographis paniculata, Boerhavia diffusa, Azhadirachta indica, Aristolochia indica, Aegle marmelos, Cyperus rotundus, Hemedesmus indicus, Trichosanthes dioica, Santalum alba, Terminalia arjuna, Woodfordia fruiticosa, Glycerrhiza glabra, Mucuna pruriens, Myrica nagi, Plumbago rosea, Inula racemosa, Zingiber officinalis, Piper longum* and *Piper nigrum* in an amount in the range of 0 to 4 wt %, of the total weight of the composition.

Mineral Element

In an embodiment, the mineral element includes Bhasmas or calcined preparations such as Swarna Makshika bhasma, Abhraka bhasma, Loha bhasma, Vanga bhasma, Yashada Bhasma and Pravala bhasma. Alternatively, the mineral element may also be selected from a group consisting of at least one of mica, tin, lead, zinc, coral, iron and copper pyrite. In the disclosed embodiments, the bhasmas along with the herb element form bioavailable herbo-mineral complexes which are useful in treating, preventing and managing Diabetes and associated complications. In an embodiment, the mineral element further includes Shilajit. However, it is also within the scope of claims provided herewith for the herbo-mineral formulation to include, as a substitute or additionally, other similar calcined preparations or minerals without otherwise deterring from the intended function of the herbo-mineral formulation.

In an embodiment, the mineral element includes shilajit in the range of 2 to 6 wt %. In another embodiment, the mineral element includes Abhraka Bhasma is in an amount of ≤2 wt %, Vanga Bhasma is in an amount of ≤1 wt %, Yashada Bhasma is in an amount of ≤1 wt %. Pravala Bhasma is in an amount of ≤2 wt %, Loha Bhasma is in an amount of ≤2 wt % and Swarna Makshika Bhasma is in an amount of ≤2 wt %, of the total weight of the composition.

The disclosed formulation, in the various embodiments herein, may further include a suitable excipient. The suitable excipients include solvents, binders, lubricants, herbal carriers, oils and salts that are generally known in the art. In a preferred embodiment, the excipient includes acacia gum.

Further, the amount of herb element and mineral element that may be included in the various embodiments of the disclosed formulation may be in the range of 0 to 10 wt %. In an embodiment, the formulation includes *Salacia chinensis* (4 to 8 wt %), *Gymnema sylvestre* (4 to 8 wt %), *Emblica officinalis* (2 to 6 wt %), *Eugenia jambolana* (4 to 8 wt %), *Curcuma longa* (3 to 7 wt %), *Commiphora mukul* (Guggulu) (3 to 7 wt %), *Tinospora cordifolia* (3 to 7 wt %), Shilajit (2 to 6 wt %), Abhraka Bhasma (≤2 wt %), Vanga Bhasma (≤1 wt %), Yashada Bhasma (≤1 wt %), Pravala Bhasma (≤2 wt %), Loha Bhasma (≤2 wt %) and Swarna Makshika Bhasma (≤2 wt %), of the total weight of the composition.

In another embodiment, the formulation further includes at least one of *Withania somnifera, Terminalia chebula, Terminalia bellerica, Andrographis paniculata, Boerhavia diffusa, Azhadirachta indica, Aristolochia indica, Aegle marmelos, Cyperus rotundus, Hemedesmus indicus, Trichosanthes dioica, Santalum alba, Terminalia arjuna, Woodfordia fruiticosa, Glycerrhiza glabra, Mucuna pruriens, Myrica nagi, Plumbago rosea, Inula racemosa, Zingiber officinalis, Piper longum* and *Piper nigrum*, wherein each of the ingredients may be included in the range of 1 to 4 wt % of the total weight of the composition.

Further, the amount of gum acacia may be any amount suitable to perform the activity of an excipient. In an embodiment, the formulation may include gum acacia in the range of 0 to 50 mg per 500 mg of the formulation, preferably 10 wt % of the total weight of the composition.

However, it is apparent that slight variations in the amount of the ingredients may be performed without otherwise deterring from the intended function of the herbo-mineral formulation.

The herbo-mineral formulation disclosed herein may be formulated in various dosage forms such that it is suitable for oral administration. The herbo-mineral formulation may be in the form of tablets, pellets, lozenges, granules, capsules, solutions, emulsions, suspensions, or any other form suitable for use. All the quantities of ingredients expressed in weight percentages (wt %) in the various embodiments herein are based on the total weight of the composition. In an embodiment, the herbo-mineral formulation is formulated in the form of tablets, preferably 500 mg tablets. For example: Table 1A depicts the quantities of each ingredient in a 500 mg tablet. Further disclosed herein, is a tablet for treating/preventing/managing diabetes and associated complications. In an embodiment, the tablet is a 500 mg tablet having herb element, mineral element and an excipient as depicted in Table 1A.

TABLE 1A

Each 500 mg tablet includes:

| NO | SANSKRIT NAME | SCIENTIFIC NAME | QUANTITY (mg) | Conc. (wt %) |
|---|---|---|---|---|
| 1 | Ekanayaka dry root | *Salacia chinensis* | 30 | 6 |
| 2 | Ashvagandha dry root | *Withania somnifera* | 10 | 2 |
| 3 | Hareetakee dry fruit | *Terminalia chebula* | 10 | 2 |
| 4 | Vibhitaki dry fruit | *Terminalia bellerica* | 10 | 2 |
| 5 | Meshashrngi dry leaves | *Gymnema sylvestre* | 30 | 6 |
| 6 | Amalaki dry fruit | *Emblica officinalis* | 20 | 4 |
| 7 | Kiratatikta dry plant | *Andrographis paniculata* | 10 | 2 |
| 8 | Punarnava dried root | *Boerhavia diffusa* | 10 | 2 |
| 9 | Nimba dry bark | *Azhadirachta indica* | 10 | 2 |
| 10 | Ishvari dry root | *Aristolochia indica* | 10 | 2 |
| 11 | Bilva dry root | *Aegle marmelos* | 10 | 2 |
| 12 | Mustaka dry root | *Cyperus rotundus* | 10 | 2 |
| 13 | Sariva dry root | *Hemedesmus indicus* | 10 | 2 |
| 14 | Patola dry plant | *Trichosanthes dioica* | 10 | 2 |
| 15 | Chandana dry heartwood | *Santalum alba* | 10 | 2 |
| 16 | Arjuna dry bark | *Terminalia arjuna* | 10 | 2 |
| 17 | Dhataki dry flower | *Woodfordia fruiticosa* | 10 | 2 |
| 18 | Yashtimadhu dry root | *Glycerrhiza glabra* | 10 | 2 |
| 19 | Kapikacchu dry seeds | *Mucuna pruriens* | 10 | 2 |
| 20 | Katphala dry bark | *Myrica nagi* | 10 | 2 |
| 21 | Jambu dry seeds | *Eugenia jambolana* | 30 | 6 |
| 22 | Shuddha Chitraka dryroot | *Plumbago rosea* | 10 | 2 |
| 23 | Haridra dry rhizome | *Curcuma longa* | 25 | 5 |
| 24 | Guduchi dry stem | *Tinospora cordifolia* | 25 | 5 |
| 25 | Pushkaramula dry root | *Inula racemosa* | 10 | 2 |
| 26 | Shunthi dry rhizome | *Zingiber officinalis* | 10 | 2 |
| 27 | Pippali dry fruit | *Piper longum* | 10 | 2 |
| 28 | Maricha dry fruit | *Piper nigrum* | 10 | 2 |
| 29 | Abhraka Bhasma | Incinerated mica | 05 | 1 |
| 30 | Vanga Bhasma | Incinerated tin | 05 | 1 |
| 31 | Yashada Bhasma | Incinerated Zinc | 2.5 | 0.5 |
| 32 | Pravala Bhasma | Incinerated coral | 2.5 | 0.5 |
| 33 | Loha Bhasma | Incinerated iron | 05 | 1 |
| 34 | Swarna MakshikaBhasma | Incinerated copper pyrite | 05 | 1 |

TABLE 1A-continued

Each 500 mg tablet includes:

| NO | SANSKRIT NAME | SCIENTIFIC NAME | QUANTITY (mg) | Conc. (wt %) |
|---|---|---|---|---|
| 35 | Shilajatu | Asphaltum | 20 | 4 |
| 36 | Guggulu oleo gum resin | Commiphora mukul | 25 | 5 |
| 37 | Excipient | Gum acacia | 50 | 10 |

Method

Disclosed herein are embodiments of a method of preparing the herbo-mineral formulation. In an embodiment, the method includes, levigating bhasmas, Guggulu and shilajit in a grinder;
adding finely powdered herbs into the grinder; and
adding grinding decoction while continuing grinding to obtain a ground mass.

The bhasmas include at least one of Abhraka Bhasma, Vanga Bhasma, Yashada bhasma, Pravala Bhasma, Loha Bhasma and Swarna Makshika Bhasma. The mixture of bhasmas, Guggulu and Shilajit may be in semi-solid form. In an embodiment, the levigation may be performed for a duration of around 3 hours.

Further, the finely powdered herbs include finely powdered dried root of *Salacia chinensis, Withania somnifera, Boerhavia diffusa, Aristolochia indica, Aegle marmelos, Cyperus rotundus, Hemedesmus indicus, Glycerrhiza glabra, Inula racemosa* and *Plumbago rosea*; dried fruits of *Terminalia chebula, Terminalia bellerica, Emblica officinalis, Piper longum* and *Piper nigrum*; dried bark of *Azhadirachta indica, Myrica nagi* and *Terminalia arjuna*; dried plant of *Androgaphis paniculata* and *Trichosanthes dioica*; dried leaves of *Gymnema sylvestre*; dried heartwood of *Santalum alba*; dried flowers of *Woodfordia fruiticosa*; dried seeds of *Mucuna pruriens* and *Eugenia jambolana*; dried rhizome of *Curcuma longa* and *Zingiber officinalis*; and dried stem of *Tinospora cordifolia*. In an embodiment, finely powdered herbs may be obtained by powdering and sieving the herb components at 80 mesh.

The grinding decoction is a decoction of the following grinding herbs: *Salacia chinensis, Cedrus deodara, Tribulus terrestris, Acacia catechu, Androgaphis paniculata, Pterocarpus marsupium, Ocimium sanctum, Adhatoda vasica, Aegle marmelos, Carum carvi, Trigonella foenum graecum, Momordia charantia* and *Araca catechu*. The decoction may be obtained by any method of decocting generally known in the field. In an embodiment, the method of preparation of grinding decoction further includes, soaking the grinding herbs i.e. powdered dry root of *Salacia chinensis*, dry heartwood of *Cedrus deodara*, dry fruit of *Tribulus terrestris*, dry heartwood of *Acacia catechu*, dry plant of *Androgaphis paniculata*, dry heartwood of *Pterocarpus marsupium*, dry leaves of *Ocimium sanctum*, dry leaves of *Adhatoda vasica*, dry leaves of *Aegle marmelos*, dry fruits of *Carum carvi*, dry seeds of *Trigonella foenum graecum*, fresh fruit of *Momordia charantia* and dry seed of *Araca catechu*; and concentrating.

In another embodiment, soaking may be performed by soaking the grinding herbs in 16 parts of water overnight. In a further embodiment, concentrating may be performed by boiling at high temperature, preferably about 80 to 85 degree Celsius, until ⅛th of the liquid remains. Concentration may be confirmed with the help of Brix meter.

Figure 2:
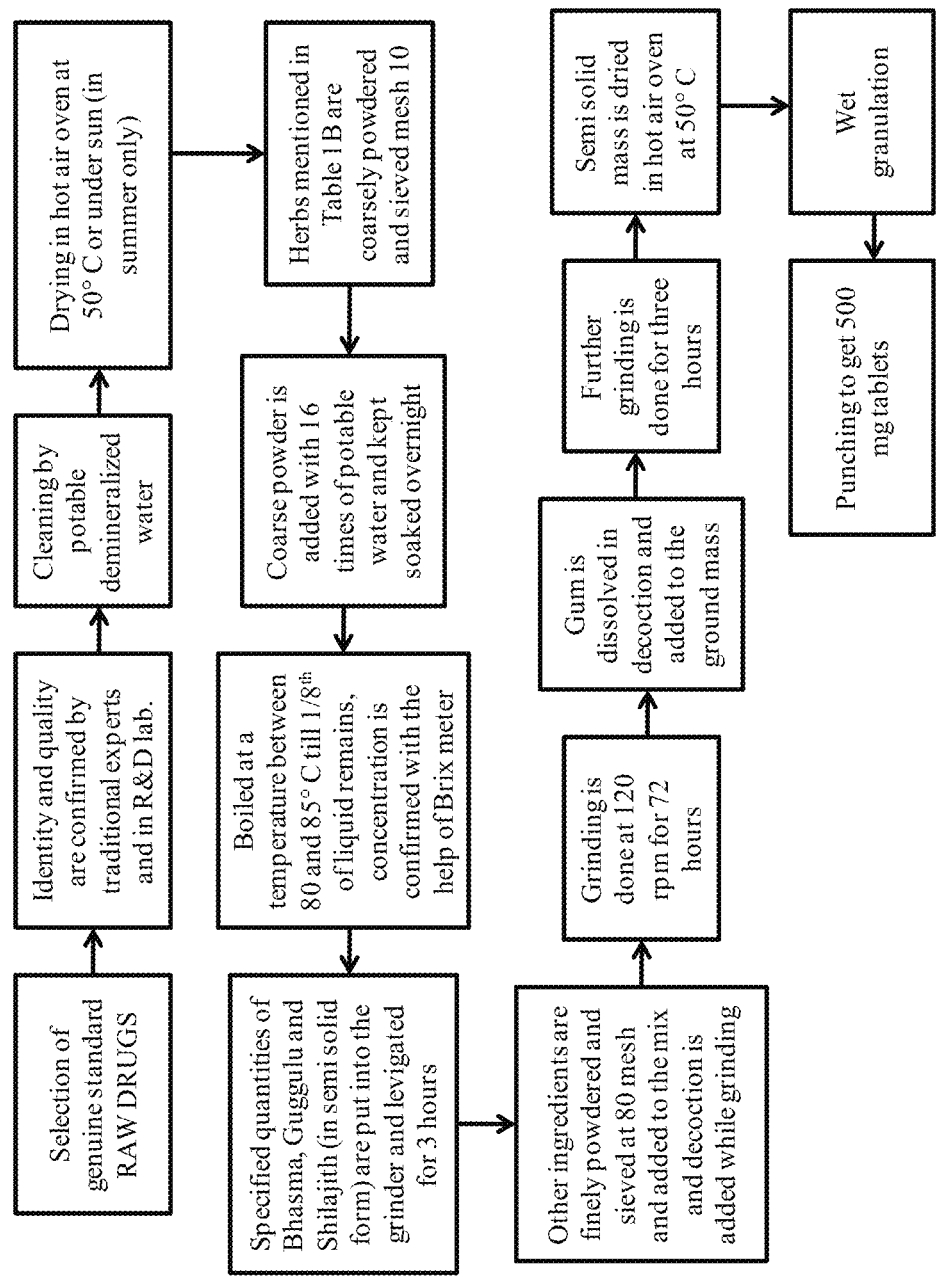
FIG. 2 depicts a flowchart for the preparation of fortified tablets.

Further, once the grinding decoction is added, grinding is continued. In an embodiment, grinding is continued for about 72 hours, preferably at 120 rpm, to obtain a ground mass. In an embodiment, the method of preparation may further include adding excipient to the ground mass, wherein gum acacia may be added to the ground mass by dissolving in the grinding decoction while continuing grinding for 3 hours to obtain a semisolid mass. The method of preparation may further include drying at 50 degree Celsius, preferably in a hot air oven, wet granulating, punching to obtain 500 mg tablets. FIG. 2 depicts a flowchart for the preparation of fortified tablets. Table 1B depicts the Herb ingredients required for grinding (grinding herbs) in one of the preferred embodiments.

TABLE 1B

List of Grinding herbs
Decoction of following herbs:

| 1 | Ekanayaka dry root | Salacia chinensis | 1 part |
| 2 | Devadaru dry heartwood | Cedrus deodara | 1 part |
| 3 | Gokshura dry fruit | Tribulus terrestris | 1 part |
| 4 | Khadira dry heartwood | Acacia catechu | 1 part |
| 5 | Kiratatikta dry plant | Androgaphis paniculata | 1 part |
| 6 | Asana dry heartwood | Pterocarpus marsupium | 1 part |
| 7 | Tulasi dry leaves | Ocimium sanctum | 1 part |
| 8 | Vasa dry leaves | Adhatoda vasica | 1 part |
| 9 | Bilva dry leaves | Aegle marmelos | 1 part |
| 10 | Krshna Jeeraka dry fruits | Carum carvi | 1 part |
| 11 | Methika dry seeds | Trigonella foenum graecum | 1 part |
| 12 | Karavellaka fresh fruit | Momordia charantia | 1 part |
| 13 | Puga dry seed | Araca catechu | 1 part |
| 14 | Jala | Water | 208 parts |
|  | Avashesha (Reduced to) |  | ⅛ part of water |

The bhasmas that are used in the various embodiments of the disclosed herbo-mineral formulation may be prepared by methods that are generally known in the field. Bhasmas may be prepared by selecting genuine standard minerals as starting material such as Swarna makshika, Mica, Iron, tin, zinc etc; drying in a hot air oven; purifying the mineral by triturating, quenching, boiling etc; triturating with herbal decoction; preparing into discs; drying of discs; preparing sharavasam puta, subjecting Sharavasam puta to Gaja puta, and powdering of discs once cooled. In an embodiment, the method is repeated 30 times till bhasma is obtained.

Figure 1C:
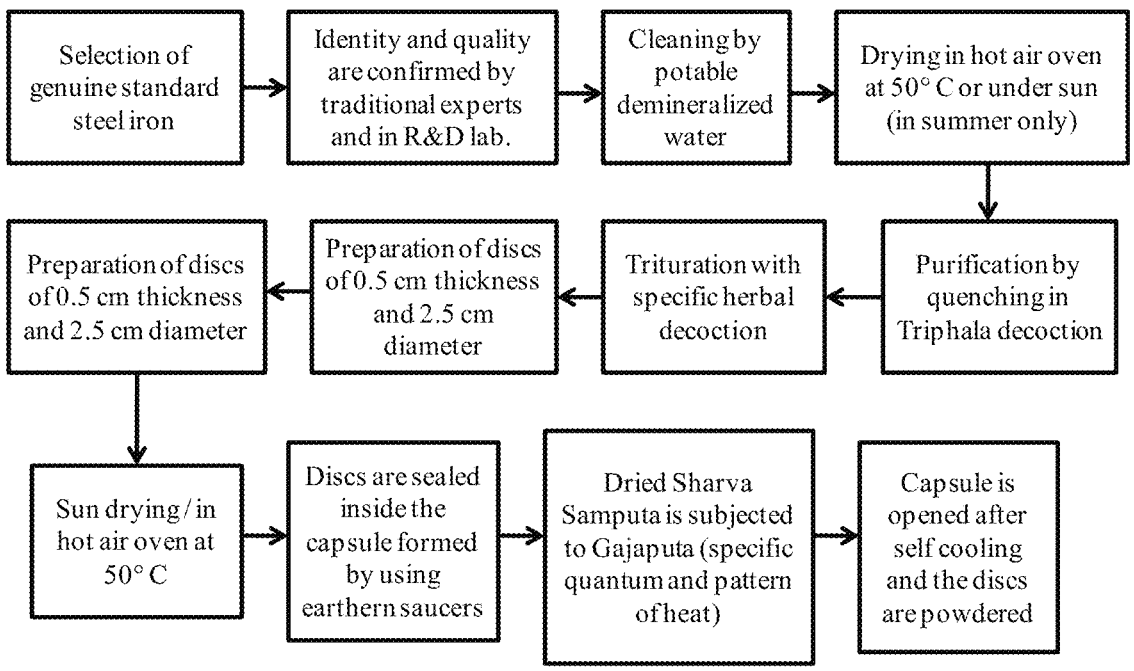
FIG. 1(c) depicts a flowchart for the preparation of Loha Bhasma.
Figure 1D:
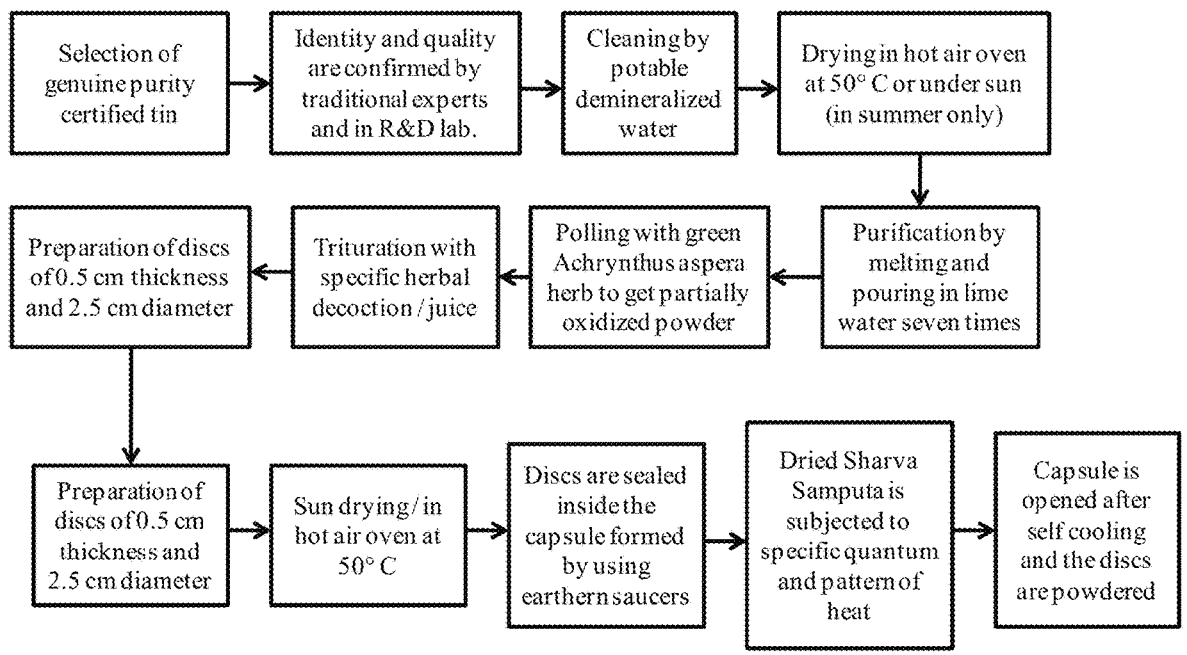
FIG. 1(d) depicts a flowchart for the preparation of Vanga Bhasma.
Figure 1E:
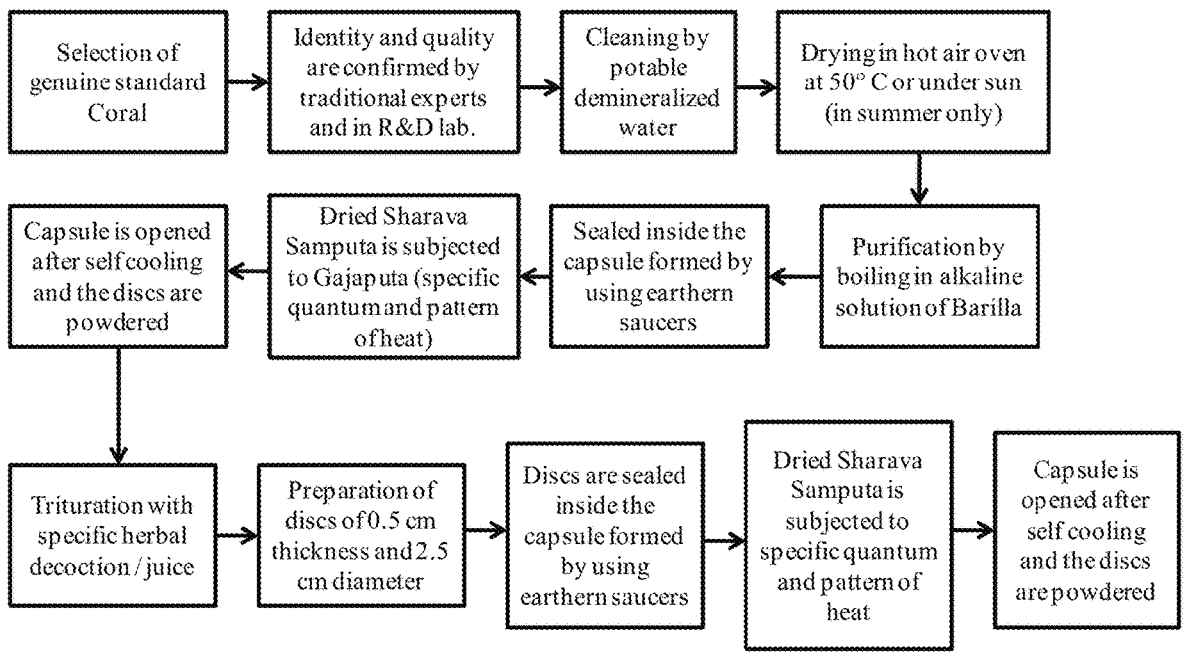
FIG. 1(e) depicts a flowchart for the preparation of Pravala Bhasma.
Figure 1F:
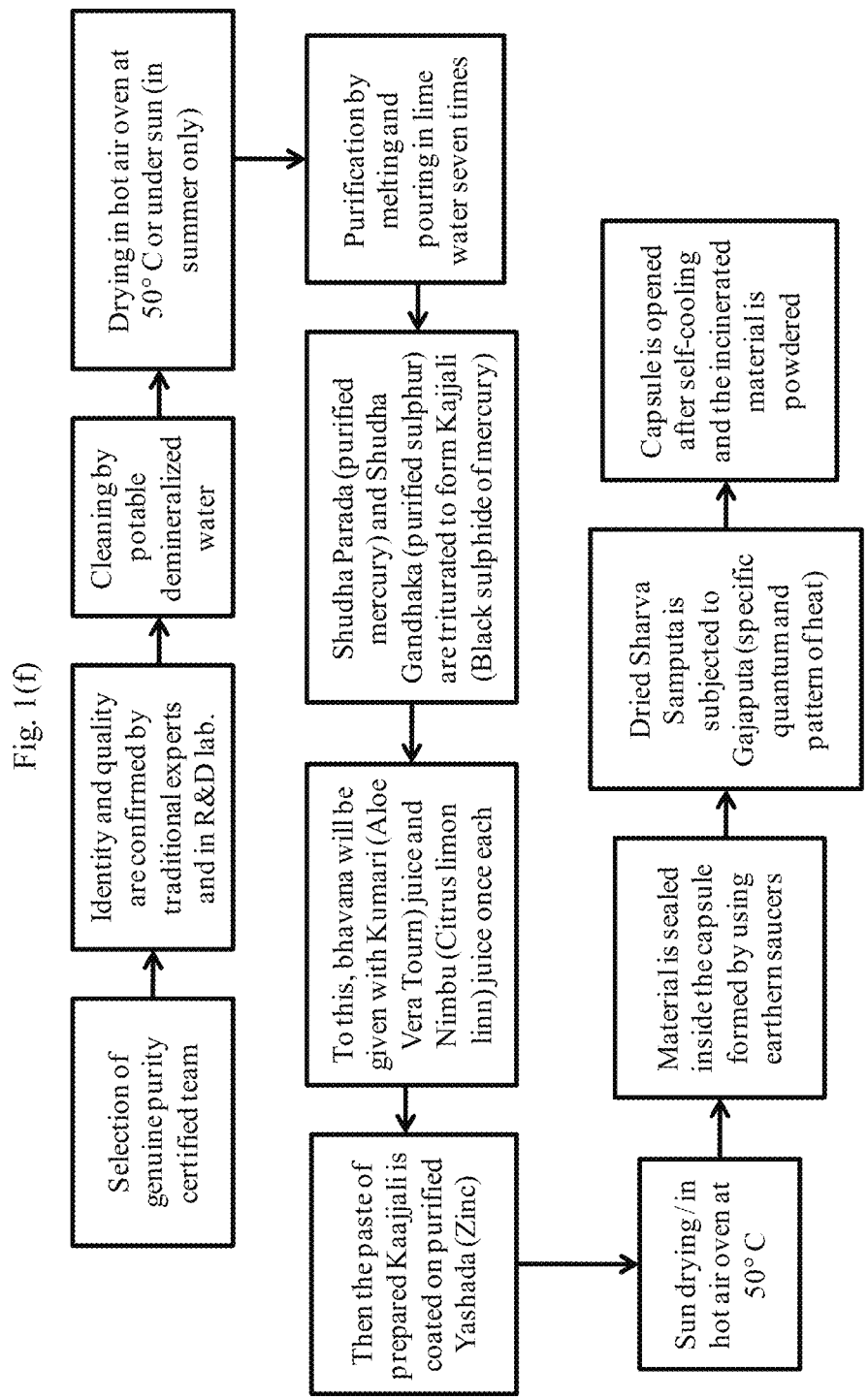
FIG. 1(f) depicts a flowchart for the preparation of Yashada Bhasma.

The starting materials used in the preparation of bhasmas may include standard minerals generally used in the field. In an embodiment, the preparation of Swarna Makshika Bhasma includes swarna makshika as the starting material. FIG. 1(a) depicts a flowchart for the preparation of Swarna Makshika Bhasma using swarna makshika as the starting material. In an embodiment, the preparation of Abhraka Bhasma includes Mica as the starting material. FIG. 1 (b) depicts a flowchart for the preparation of Abhraka Bhasma using Mica as the starting material. In an embodiment, the preparation of Loha Bhasma includes steel iron as the starting material. FIG. 1(c) depicts a flowchart for the preparation of Loha Bhasma using steel iron as the starting material. In another embodiment, the preparation of Vanga Bhasma includes Tin and lead as the starting material. FIG. 1(d) depicts a flowchart for the preparation of Vanga Bhasma using alloys of Tin and lead as the starting material. In an embodiment, the preparation of Pravala Bhasma includes Coral as the starting material. FIG. 1(e) depicts a flowchart for the preparation of Pravala Bhasma using Coral as the starting material. In an embodiment, the preparation of Yashada Bhasma includes Zinc as the starting material. FIG. 1(f) depicts a flowchart for the preparation of Yashada Bhasma using Zinc as the starting material.

The purification, or shodhana, of the mineral may be performed by generally known methods in the field. In an embodiment, the purification may be by mixing the mineral, such as swarna makshika, with rocksalt and lemon juice and heating strongly till partially oxidized into reddish powder which may further be used in the preparation of Swarna makshika Bhasma. In another embodiment, the purification may be by quenching a mineral such as micain Cow's milk, wherein it is further used in the preparation of Abhraka Bhasma.

In yet another embodiment, the purification may be by quenching a mineral such as steel iron in Triphala decoction, which is further used in the preparation of Loha Bhasma. In yet another embodiment, the purification may be by melting and pouring the mineral for example Tin or Zinc in lime water, preferably seven times, which is further used in the preparation of Vanga Bhasma or Yashada Bhasma, respectively.

Further, in an embodiment, the process of purification may include boiling mineral such as Coralin an alkaline solution of Barilla, which is further used in the preparation of Pravala Bhasma.

The herbal decoction/juices used for triturating may be any herbal decoction/juice that is generally used for triturating in the preparation of bhasmas. For example, the herbal decoction/juice may include triphala, lemon juice, Gomutra (cow's urine) etc. The following are herbal decoction/juices that may be used in trituration while preparing various bhasmas:

Table A illustrates the ingredients of Herbal decoction used for trituration while preparing Abhraka Bhasma.

TABLE A

| | Decoction of following herbs: | | |
|---|---|---|---|
| 1. | Amalaki dried fruit | *Emblica officinalis* | 1 part |
| 2. | Hareetaki dried fruit | *Terminalia chebula* | 1 part |
| 3. | Vibheetaki dried fruit | *Terminalia bellerica* | 1 part |
| 4. | Musta dried rhizome | *Cyperus rotundus* | 1 part |
| 5. | Vata dried root bark | *Ficus bengalensis* | 1 part |

TABLE A-continued

| | Decoction of following herbs: | | |
|---|---|---|---|
| 6. | Haridra dried rhizome | *Curcuma longa* | 1 part |
| 7. | Jala | Water | 96 parts |
| | Avashesha (Reduced to) | | ⅛ part of liquid |

Table B illustrates the ingredients of Herbal juice used for trituration while preparing Abhraka Bhasma.

TABLE B

| | Juice of following herbs: | | |
|---|---|---|---|
| 1. | Kasamarda fresh leaves | *Cassia occidentalis* | 1 part |
| 2. | Tambula fresh leaves | *Piper betle* | 1 part |
| 3. | Vasa fresh leaves | *Adhatoda vasica* | 1 part |
| 4. | Amalaki fresh fruit | *Emblica officinalis* | 1 part |
| 5. | Matsyakshi fresh plant | *Alternathera sessilis* | 1 part |
| 6. | Tanduleeyaka fresh plant | *Amaranthus spinosus* | 1 part |
| 7. | Eranda fresh leaves | *Ricinus communis* | 1 part |
| 8. | Arka fresh leaves | *Calotropis precera* | 1 part |

Table C illustrates the ingredients of Herbal decoction used for trituration while preparing Vanga Bhasma.

TABLE C

| | Decoction of following herbs: | | |
|---|---|---|---|
| 1. | Amalaki | *Emblica officinalis* | 1 part |
| 2. | Hareetaki | *Terminalia chebula* | 1 part |
| 3. | Vibheetaki | *Terminalia bellerica* | 1 part |
| 4. | Haridra dried rhizome | *Curcuma longa* | 1 part |
| 5. | Jala | Water | 64 parts |
| | Avashesha (Reduced to) | | ⅛ part of liquid |

Table D illustrates the ingredients of Herbal juice used for trituration while preparing Vanga Bhasma.

TABLE D

| | Juice of following herbs: | | |
|---|---|---|---|
| 1. | Kumari fresh leaves | *Aloe vera* | 1 part |

Table E illustrates the ingredients of Herbal juice used for trituration while preparing Yashada Bhasma

TABLE E

| | Juice of following herbs: | | |
|---|---|---|---|
| 1. | Kumari fresh leaves | *Aloe vera* | 1 part |
| 2. | Nimbu fresh fruit | *Citrus limon* Linn. | 1 part |

Table F illustrates the ingredients of Herbal decoction used for the trituration to prepare Loha Bhasma.

TABLE F

| | Decoction of following herbs: | | |
|---|---|---|---|
| 1. | Amalaki | *Emblica officinalis* | 1 part |
| 2. | Hareetaki | *Terminalia chebula* | 1 part |
| 3. | Vibheetaki | *Terminalia bellerica* | 1 part |
| 4. | Varuna | *Crataeva nurvala* | 1 part |
| 5. | Punarnava | *Boerhavia diffua* | 1 part |
| 6. | Kanchanara | *Bauhinia variegata* | 1 part |
| 7. | Gomutra | Cow urine | 48 parts |
| 8. | Jala | Water | 48 parts |
| | Avashesha (Reduced to) | | ⅛ part of liquid |

Table G illustrates the ingredients of Herbal juice used for trituration while preparing Swarna Makshika Bhasma.

TABLE G

| Juice of following herbs: | | | |
|---|---|---|---|
| 1. | Nimbu fresh fruit | Citrus limon Linn. | 1 part |

Treatment

Disclosed herein are embodiments of the method of treating/preventing/managing Diabetes and Diabetes associated complications. The embodiments disclosed herein are instrumental in reducing elevated fasting and post prandial blood sugar levels and elevated HbA1C levels.

In an embodiment, the method includes administering to a patient a composition as described in any of the embodiments disclosed herein. In an embodiment, the patient may be any individual in need of such treatment including ones having/expected or suspected of having Diabetes. Further, the patient may also be any individual having/suspected of having complications associated with Diabetes such as hyperglycemia, hyperlipidemia, etc. The patient may also include any individual showing diabetes symptoms such as individuals having ≥5.7 wt % of HdA1C levels, ≥100 mg/dl of FBS, ≥140 mg/dl of OGTT etc.

In a preferred embodiment, the method includes administering to a patient a composition having herb element, mineral element and suitable excipient, wherein the herb element includes Salacia chinensis (4 to 8 wt %), Gymnema sylvestre (4 to 8 wt %), Emblica officinalis (2 to 6 wt %), Eugenia jambolana (4 to 8 wt %), Curcuma longa (3 to 7 wt %), Commiphora mukul (Guggulu) (3 to 7 wt %), Tinospora cordifolia (3 to 7 wt %) and at least one of herb selected from Withania somnifera, Terminalia chebula, Terminalia bellerica, Andrographis paniculata, Boerhavia diffusa, Azhadirachta indica, Aristolochia indica, Aegle marmelos, Cyperus rotundus, Hemedesmus indicus, Trichosanthes dioica, Santalum alba, Terminalia arjuna, Woodfordia fruiticosa, Glycerrhiza glabra, Mucuna pruriens, Myrica nagi, Plumbago rosea, Inula racemosa, Zingiber officinalis, Piper longum and Piper nigrum; and the mineral element includes Shilajit (2 to 6 wt %) and at least one of bhasma selected from Abhraka Bhasma (≤2 wt %), Vanga Bhasma (≤1 wt %), Yashada Bhasma (≤1 wt %), Pravala Bhasma (≤2 wt %), Loha Bhasma (≤2 wt %) and Swarna Makshika Bhasma (≤2 wt %).

In an embodiment, the disclosed formulation may also be used to prevent the complications of diabetes like retinopathy, neuropathy, nephropathy and vascular diseases.

In a further embodiment, the disclosed formulation may be used to reduce enhanced levels of lipid/cholesterol levels, tissue phosphatases and tissue transaminases in the diabetic tissues. Furthermore, in an embodiment, the disclosed formulation may be instrumental in reversing the glycogen and protein depletion that is generally observed in tissues of diabetic subjects.

The disclosed method of treatment may be used as a primary line of treatment or as an adjunct to other diabetic treatment. In an embodiment, the disclosed formulation may be used to stimulate regeneration of 3 cells of islets of pancreas. In an embodiment, the disclosed formulation may be useful as a hypoglycemic, hypolipidemic, cytoprotective and immunomodulatory agent. In an embodiment, the disclosed formulation may be used to improve the quality of life of Diabetic patients. Further, in an embodiment, the disclosed formulation may be instrumental reducing FBS, PPBS, HbA1C level and also improving clinical symptoms One of the embodiments relating to the formulations disclosed herein (also referred as Test product) was further tested for efficacy at 3 levels Experimental study, Clinical study and Quality of Life (QOL) assessment, as described hereunder by way of examples. The embodiment is further described by reference to the following examples by way of illustration only, and should not be construed to limit the scope of the claims provided herewith. It will be apparent to those skilled in the art that many modifications, both to materials and methods, may be practiced without departing from the scope of the claims.

Example 1: Experimental Study

The aim of this study was to analyze the action of test product on blood glucose, lipids, tissue proteins, pancreatic amylase and islet cells of pancreas in alloxan induced diabetic rats.

Experiment Details:

Animals: Albino rats of Wistar strain, of either sex, fed with standard rat pellets and water ad libitum.

Experimental diabetes: Diabetes was induced by a single intra-peritoneal injection of 5% alloxan monohydrate dissolved in 0.9% saline, at a dose of 200 mg/kg body weight, after a 16 hour fast.

Test drug therapy: The tablets were powdered, weighed and mixed with water to form a uniform suspension, which was administered orally every morning using a gastric tube.

Figure 3:
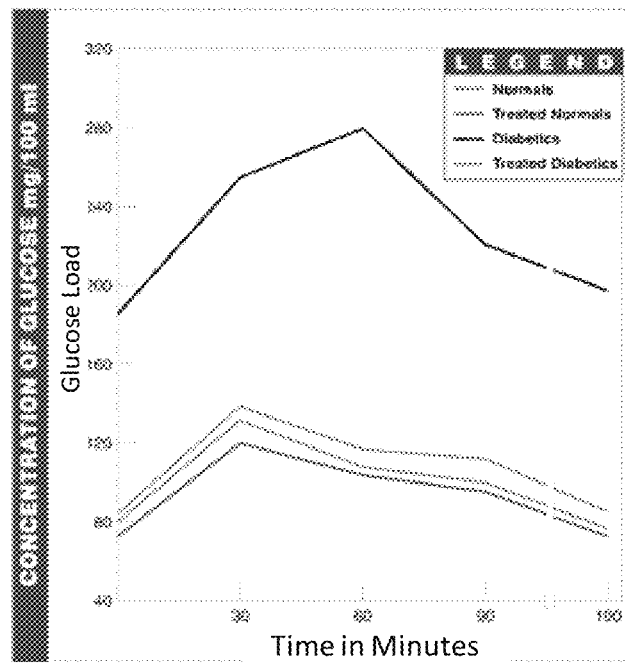
FIG. 3 is a graph depicting the results of the Oral glucose tolerance test in normal and diabetic rats treated with the embodiments disclosed herein.

Dose: 1 ml (30 mg/cc) Results:

FIG. 3 illustrates the results of the Oral glucose tolerance test in normal and diabetic rats after Test product treatment. The treated normal rats showed hypoglycemic effects, while the diabetic animals showed significant reduction in blood glucose levels.

Figure 4:
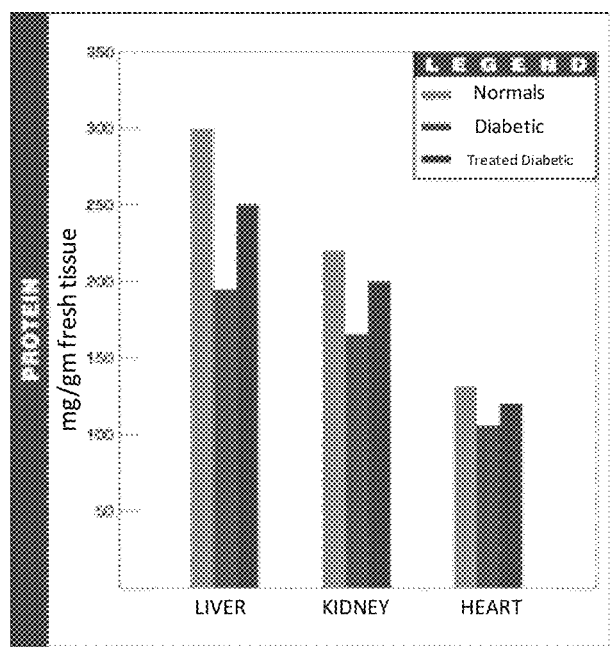
FIG. 4 is a graph depicting the effect of administering the embodiments disclosed herein on protein depletion in diabetic rats.

FIG. 4 illustrates the effect of Test product on protein depletion in diabetic rats. Protein depletion in vital organs was found reduced.

Figure 5:
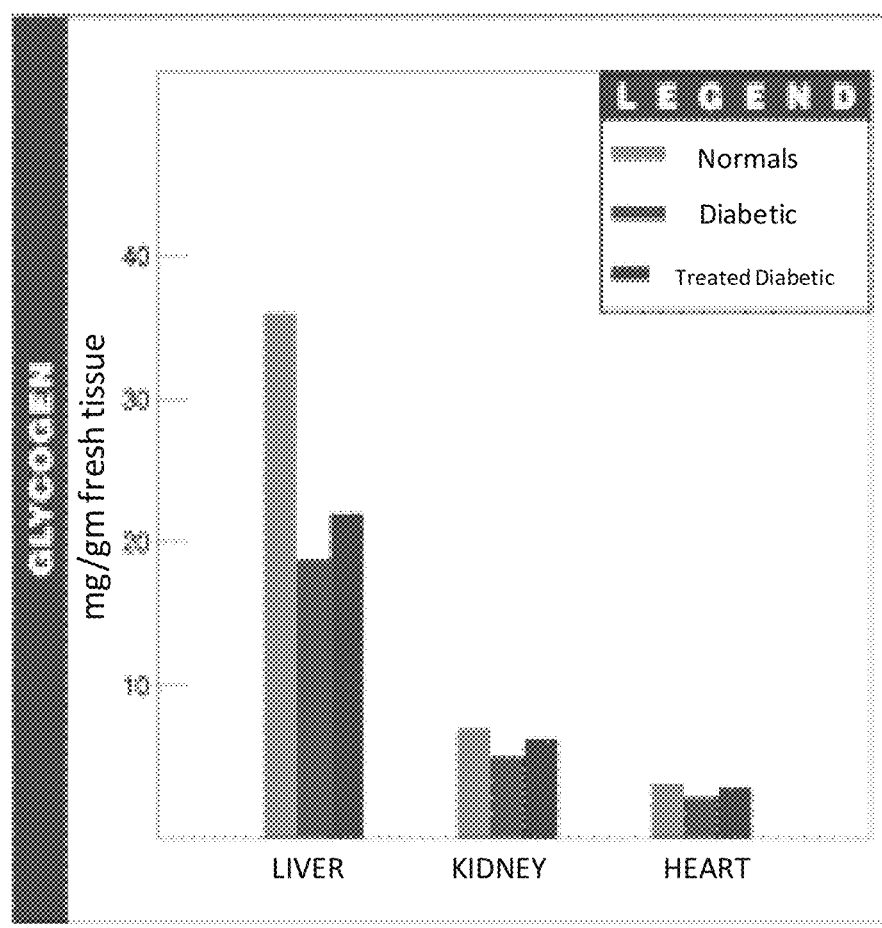
FIG. 5 is a graph depicting the reduction in tissue glycogen depletion by treatment with the embodiments disclosed herein.

FIG. 5 illustrates the effect of Test product on tissue glycogen depletion in diabetic rats. Glycogen depletion was found reduced by Test product therapy.

Figure 6:
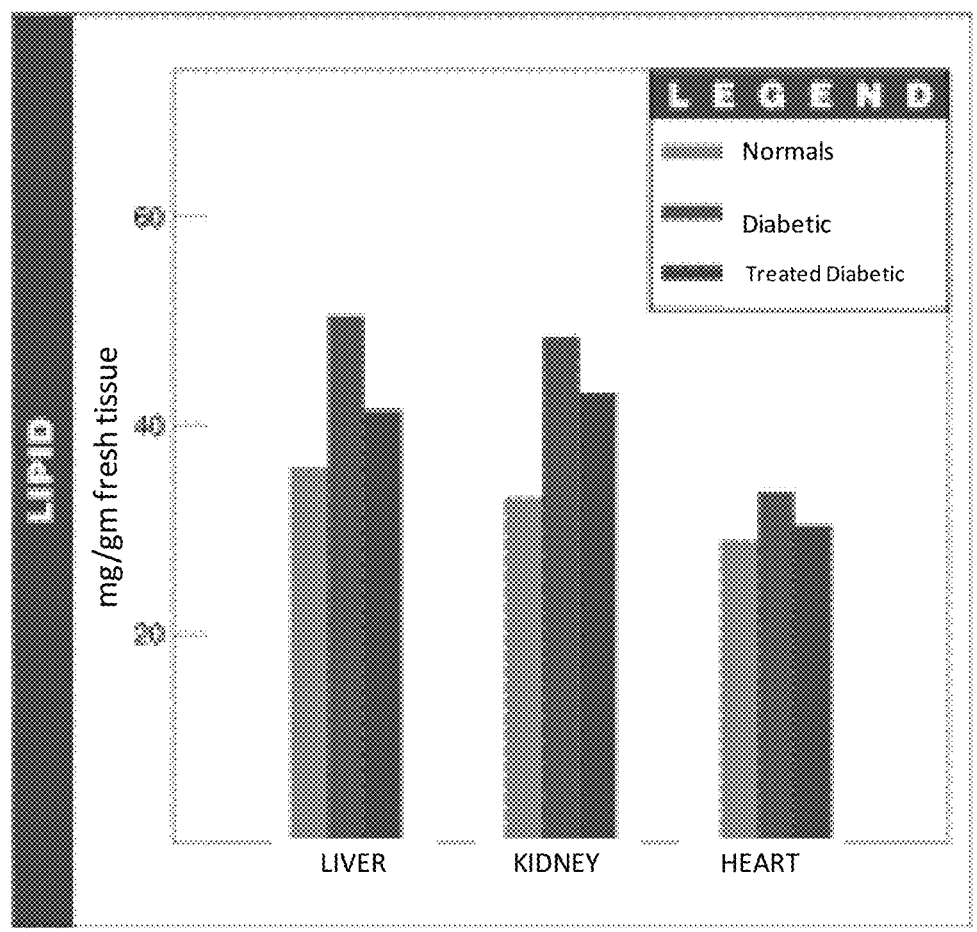
FIG. 6 depicts tissue lipids of normal and diabetic rats after treatment with the embodiments disclosed herein.

FIG. 6 illustrates the effect of Test product on tissue lipids of normal and diabetic rats. The enhanced lipid levels in the diabetic state were found to be significantly reduced after treatment.

Figure 7:
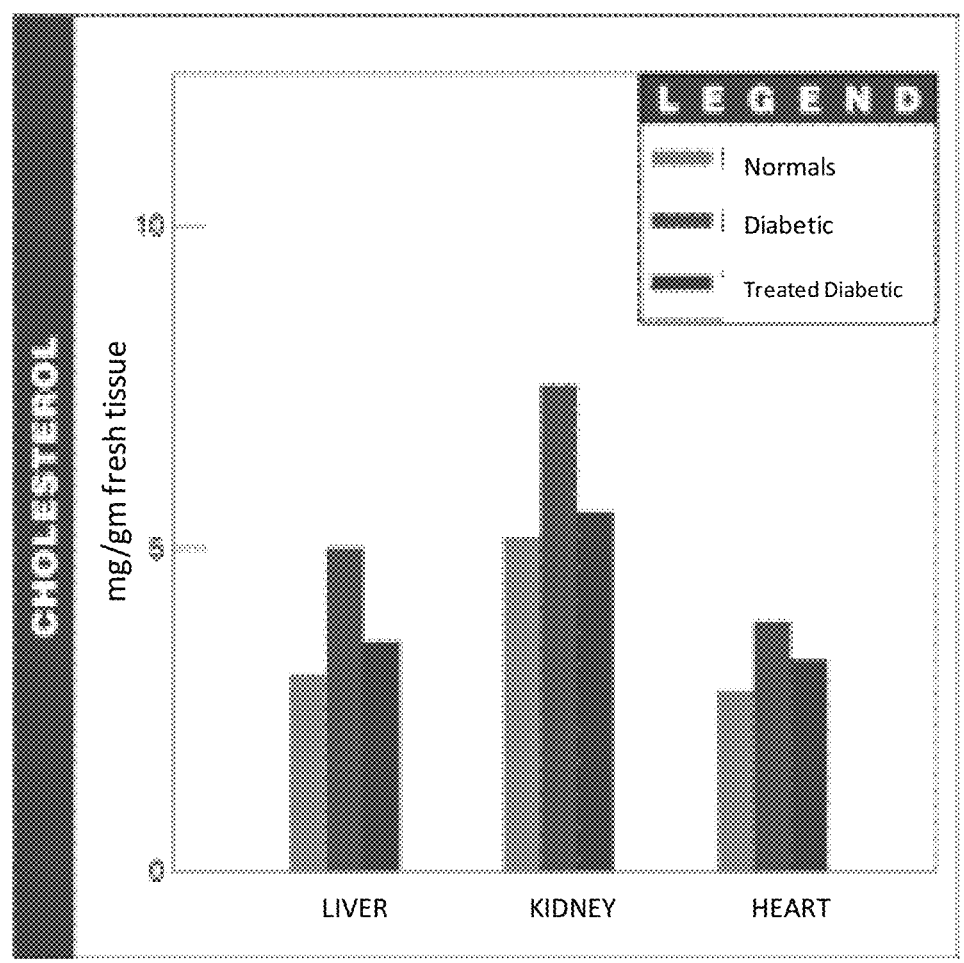
FIG. 7 depicts Cholesterol of normal and diabetic rats after treatment with the embodiments disclosed herein.

FIG. 7 illustrates the effect of Test product on Cholesterol of normal and diabetic rats. The enhanced cholesterol levels in the diabetic state were found to be markedly reduced after treatment.

Figure 8:
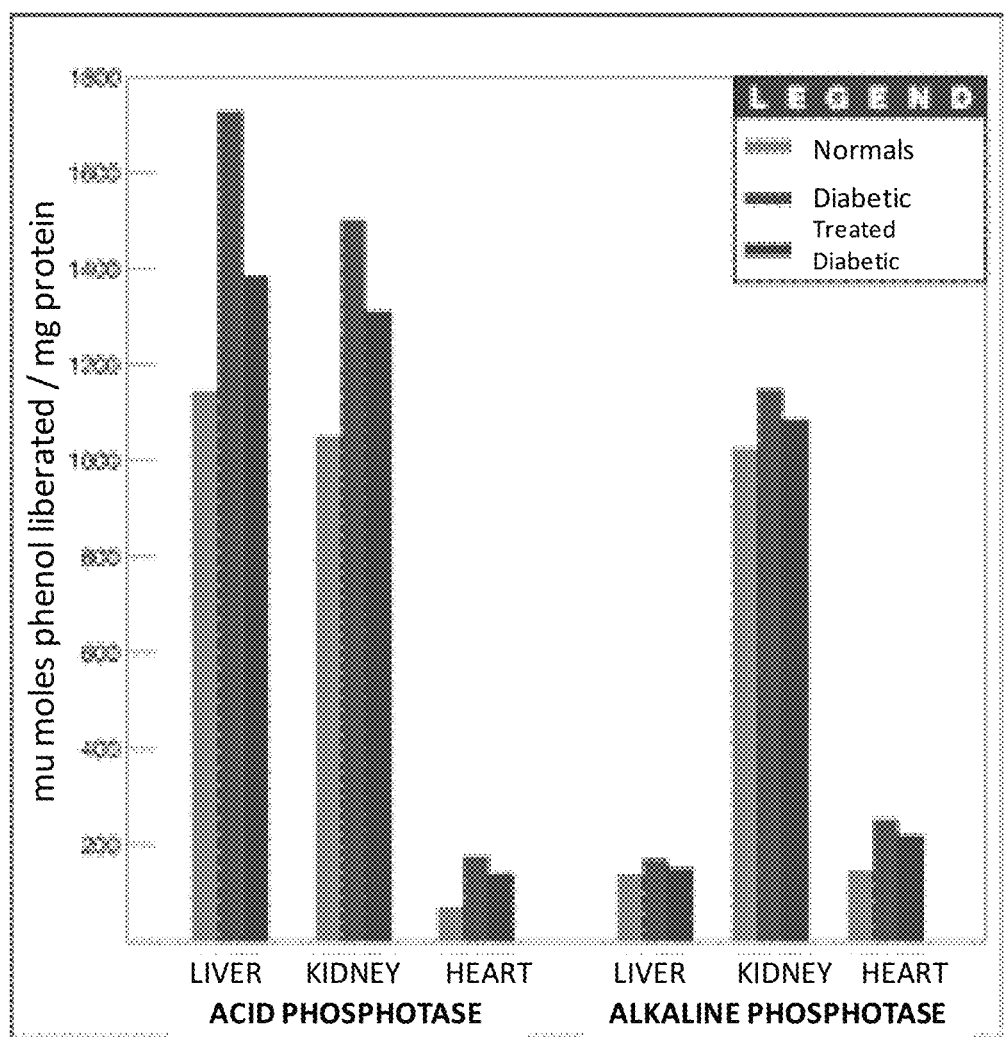
FIG. 8 depicts tissue phosphatases in rats treated with the embodiments disclosed herein.

FIG. 8 illustrates the effect of Test product on tissue phosphatases. The enhanced levels of tissue phosphatases (acid and alkaline phosphatases) and tissue transaminases (alanine and aspartate transaminases) in the diabetic tissues showed significant reduction after treatment.

Figure 9:
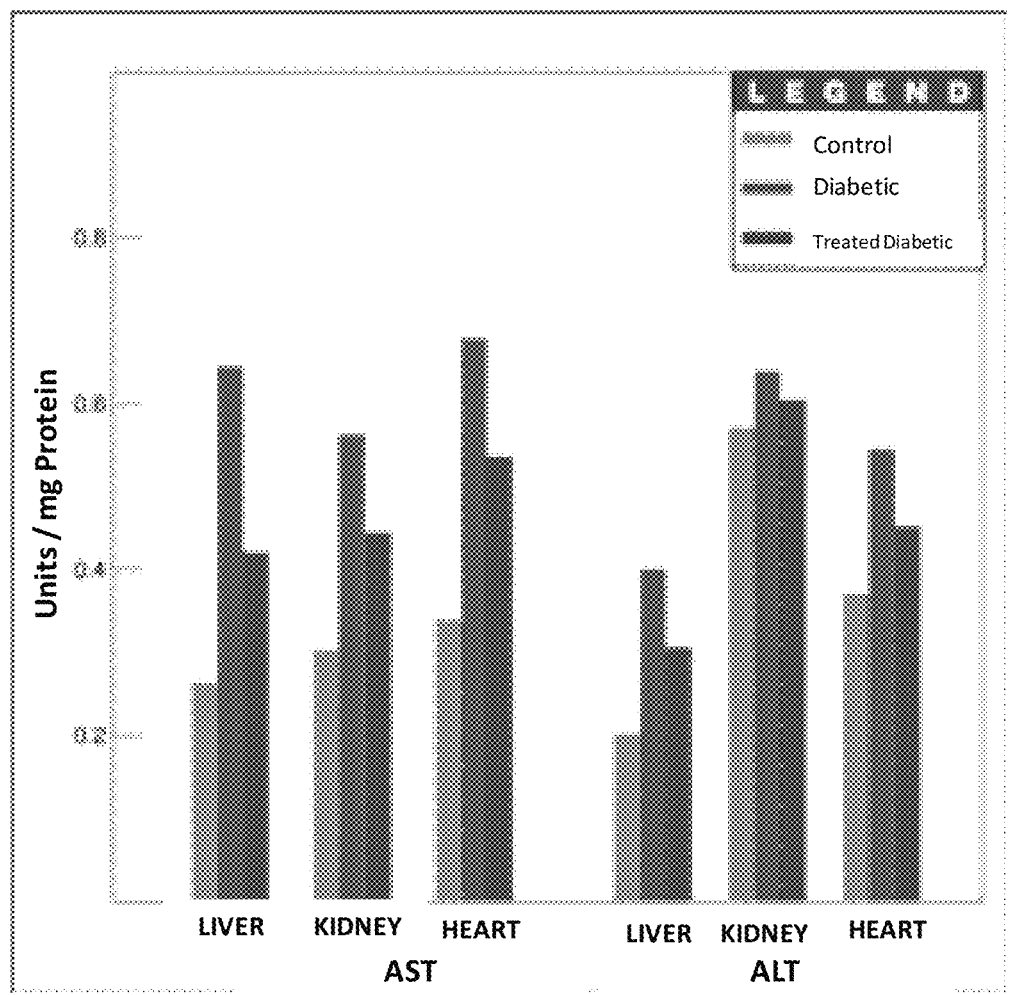
FIG. 9 depicts tissue transaminase in rats treated with the embodiments disclosed herein.

FIG. 9 illustrates the effect of Test product on tissue transaminase in diabetic rats. Pancreatic amylase activities were below normal in diabetic animals. Administration of Test product could elevate the enzyme levels, but not to normal levels.

Figure 10A:
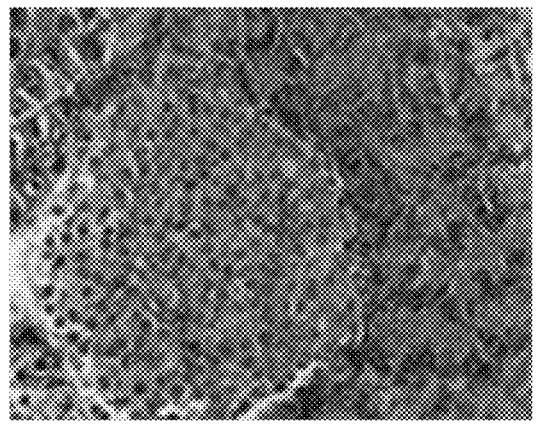
FIG. 10(a) represents a photomicrograph of Pancreatic islet from normal rats (200×) treated with the embodiments disclosed herein.
Figure 10B:
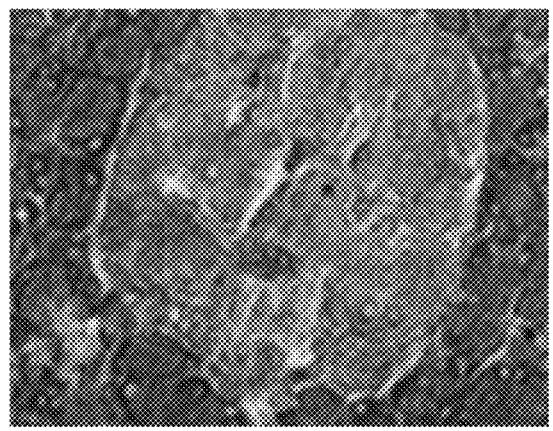
FIG. 10(b) represents a photomicrograph of Pancreatic islet from alloxan induced diabetic rats showing degranulation and necrotic B cells (300×) treated with the embodiments disclosed herein.
Figure 10C:
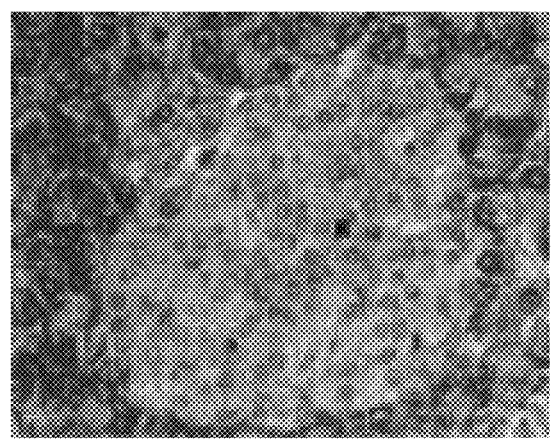
FIG. 10(c) represents a photomicrograph of pancreatic islet from diabetic rats treated with the embodiments disclosed herein, according to the embodiments herein.

FIG. 10(a), FIG. 10(b) and FIG. 10(c) illustrates the Histological studies made in pancreas of diabetic rats. The study showed islet cell de-granulation and destruction of B cells. Regeneration of B-cells and increased islet cell mass was noted in the pancreas of diabetic rats after Test product administration. FIG. 10(a) is a photomicrograph of Panreatic islet from normal rats (200×); FIG. 10(b) is a photomicrograph of Panreatic islet from alloxan induced diabetic rats showing degranulation and necrotic B cells (300×); and FIG. 10(c) is a photomicrograph of pancreatic islet from diabetic rats treated with Disclosed Formulation which is showing marked regeneration.

Example 2: Clinical Study

The aim of this clinical study was to evaluate the clinical efficacy and safety (long-term and short-term) of Test product as monotherapy and as an adjunct with other oral hypoglycemic drugs in management of NIDDM. This study helps evaluate the action of Test product on clinical and biochemical features of diabetic patients.

Study Design: This was a prospective, open, non-randomized, phase III clinical trial conducted at the Out Patient Department of Muniyal Ayurvedic Hospital and Research Centre, Manipal, India.

Materials and Methods

Inclusion Criteria: A total of 340 patients of either sex, between 30-60 years of age in whom the diagnosis of NIDDM was confirmed, and who were willing to give informed consent were included in the study. The WHO diagnosis criteria (1980) was considered for diagnosis of NIDDM (For newly diagnosed patients: FBSL >120 mg % and after 2 hours of consuming 75 grams of glucose: >180 mg %).

Exclusion Criteria: Insulin-dependent diabetes mellitus patients and NIDDM patients with acute complications of diabetes were excluded from the trial. Pregnant and lactating women, patients with concomitant severe illness necessitating other medications, patients with severe hypertension, history of severe unstable angina, myocardial infarction, CVAs, renal failure, and those patients, who were not willing to give informed consent were also excluded from the study.

Study Procedure:

Dose and Duration: Patients were advised to consume 2 tablets of Test product, thrice daily, for 3 months i.e. 2 tablets of Test product after breakfast followed by another 2 tablets after lunch, and 2 tablets after dinner.

In all the patients, blood sugar level was assessed at the time of enrolment and thereafter every month, for 3 months. All the patients had to undergo biochemical laboratory investigations. The improvement in the NIDDM symptoms was assessed using a predefined symptom scores. All patients were investigated for urine (routine and microscopic), hemogram, total leucocyte count, differential leucocyte count, serum creatinine, blood urea, serum albumin, serum globulin and lipid profile. Scale from 0 to 3 (0=absent, 1=mild, 2=moderate and 3=severe).

Primary and Secondary Endpoints: The predefined primary efficacy end points were PPBSL control and reduction in the dose of other oral hypoglycemic drugs. The PPBSL control was graded as: excellent: up to 130 mg %, good: upto 150 mg %, fair: upto 180 mg %, poor: up to 250 mg % and treatment failure: >250 mg %. The predefined secondary safety endpoints were reduced incidence of adverse reactions and overall compliance to the drug therapy.

Follow-up and Assessment: All patients were followed up for 3 months (during the treatment period) and at each follow-up visit, the patient's response to the study drug was recorded in a structured CRF. The subjective symptomatic relief and changes in the symptom score scale for each symptom were recorded during each follow-up visit.

Adverse Events: All adverse events reported or observed by patients were recorded with information about the severity, date of onset, duration and action taken regarding the study drug. Relation of adverse events to study medication was predefined as "Unrelated" (a reaction that does not follow a reasonable temporal sequence from the time of administration of the drug), "Possible" (follows a known response pattern to the suspected drug, but could have been produced by the patient's clinical state or other modes of therapy administered to the patient), and "Probable" (follows a known response pattern to the suspected drug that could not be reasonably explained by the known characteristics of the patient's clinical state).

Patients were allowed to voluntarily withdraw from the study, if they had experienced serious discomfort during the study or sustained serious clinical events requiring specific treatment. For patients withdrawing from the study, efforts were made to ascertain the reason for dropout. Non-compliance (defined as failure to take less than 80% of the medication) was not regarded as treatment failure, and reasons for non-compliance were noted.

Statistical Analysis: Statistical analysis was done according to intention-to-treat principles. The changes in various parameters from baseline values and the values after 1st, 2nd and 3rd month were analyzed by "Paired "t" Test". The minimum level of significance was fixed at 95% confidence limit and a 2-sided p value of <0.05 was considered as significant.

Results:

Assessment variables that include clinical features of diabetes mellitus like polyuria, polydipsia, polyphagia, burning sensation and lassitude were given comparative scoring and the mean scores before and after the administration of Test product supplement t were compared. Table 2 depicts the results of the action of Test product on various features of Diabetes mellitus. From the table it is clear that there is a considerable reduction in the severity of clinical features of Diabetes mellitus which is found to be statistically highly significant (P<0.001).

TABLE 2

Results of action on clinical features

| Assessment Variables | Mean ± S.D | | t value | P value |
|---|---|---|---|---|
| | BT | AT | | |
| Polyurea | 2.3 ± 0.66 | 0.30 ± 0.47 | 13.78 | P < 0.001 |
| Polydypsia | 2.1 ± 0.72 | 0.35 ± 0.48 | 14.23 | P < 0.001 |
| Polyphagia | 1.4 ± 0.75 | 0.25 ± 0.44 | 8.76 | P < 0.001 |
| Burning Sensation | 1.90 ± 0.97 | 0.55 ± 0.75 | 9.0 | P < 0.001 |
| Lassitude | 1.75 ± 0.55 | 0.45 ± 0.51 | 12.37 | P < 0.001 |

Table 3 depicts the results of the action of Test product Tablets on Blood Sugar. A significant reduction was observed in both FBS and PPBS (23.75% and 30.95% respectively). Results were also statistically highly significant at P<0.001.

TABLE 3

Results of action on Blood sugar

| Assessment Variables | Mean ± S.D | | t value | P value | % reduction |
|---|---|---|---|---|---|
| | BT | AT | | | |
| Fasting blood sugar | 126.3 ± 0.52 mg/dl | 96.3 ± 0.56 mg/dl | 12.26 | P < 0.001 | 23.75 |

TABLE 3-continued

Results of action on Blood sugar

| Assessment | Mean ± S.D | | | | % |
|---|---|---|---|---|---|
| Variables | BT | AT | t value | P value | reduction |
| Post prandial blood sugar | 290.5 ± 0.23 mg/dl | 200.6 ± 0.64 mg/dl | 11.35 | P < 0.001 | 30.95 |

Example 3: Quality of Life Study

Study design: Prospective observational study design
Sources of data:
Primary Data: Patient Case Records and interviewing the patients.
Secondary Data: Internet websites, Ayurvedic text books, Journals.
Inclusion Criteria:
All type II diabetes mellitus patients
Age 18-75 years
Patients with Diabetes Mellitus taking only Test Product tablets
Patients who agreed to sign ICF
Patients in whom the treatment pattern will not change till 3 months
Exclusion Criteria:
Type I diabetes patients.
Pregnant ladies.
Lactating women.
Chronically ill patients.
Patient who are on life style modification or on diet therapy (pre diabetic patient).
Patient who refused to be part of the study.
Study site: This study was conducted in group of patients receiving Test Product tablets for the treatment of type II diabetes mellitus in and around Udupi and Manipal region, Karnataka.
Study Duration: Total duration of the study was 6 months.
Research Instruments:
Patient Data Collection Form
DMSAT Questionnaire
QOL Questionnaire
Kuppuswamy socio-economic scale
Results:
Demographics:
Total no. of patients participated: 53
Total no. of patients completed the study: 51
Total no. of male patients: 41
Total no. of female patients: 10
Table 4 illustrates age and sex wise distribution of patients.

TABLE 4 age and sex wise distribution of patients

| No. of patients in each group | Male | Female | Total |
|---|---|---|---|
| Group 1 (36-45 years) | 7 | 1 | 8 |
| Group 2 (36-45 years) | 9 | 6 | 15 |
| Group 3 (36-45 years) | 19 | 2 | 21 |
| Group 4 (36-45 years) | 6 | 1 | 7 |
| Total | 41 | 10 | 51 |

Clinical Efficacy: Efficacy was calculated by measuring the fasting blood glucose level and HbA1c at four intervals that is on Day1, Day15, Day 30 and Day90.
Results:
Overall patient clinical data: Table 5 illustrating FBS data of overall patients shows an average reduction of 34.49% at the end of 90 days.

TABLE 5

FBS data

| Day | Mean ± SD (mg/dl) | % Reduction |
|---|---|---|
| 1 | 188.24 ± 41.39 | 34.49% |
| 15 | 167.63 ± 35.24 | |
| 30 | 149.78 ± 33.58 | |
| 90 | 123.31 ± 25.97 | |

Table 6 illustrating HbA1c data of overall patients shows an average reduction of 28.27% in 90 days.

TABLE 6

HbA1c data

| Day | Mean ± SD (mg/dl) | % Reduction |
|---|---|---|
| 1 | 8.88 ± 1.67 | 28.27% |
| 90 | 6.37 ± 0.98 | |

Table 7 depicts that a marked improvement was observed in all the parameters of patient satisfaction indicating the high acceptability of the product.

TABLE 7

Results for parameters of patient satisfaction

| | Scores | | | |
|---|---|---|---|---|
| Parameters | Day 15 | Day 30 | Day 90 | % Improvement |
| Well being | 0.32 | 0.46 | 0.62 | 48.39% |
| Glucose control | 0.33 | 0.46 | 0.61 | 45.90% |
| Life style | 0.30 | 0.41 | 0.53 | 43.40% |
| Convenience | 0.32 | 0.42 | 0.56 | 42.86% |
| Overall | 0.32 | 0.44 | 0.58 | 44.83% |

Quality of Life Study Results:
Effect of Test Drug on PCS:
Table 8 depicts that a 30.01% improvement was seen in Physical Component Score observed after 90 days of treatment with Test drug.

TABLE 8

| | Physical Component Score | |
|---|---|---|
| Day | Mean ± SD (mg/dl) | % Reduction |
| 15 | 34.58 | 30.01% |
| 30 | 41.3 | |
| 90 | 49.41 | |

Effect on Test Drug on MCS:

Table 9 depicts that a 52.52% improvement was seen in Mental Component Score after 90 days of treatment with Test product.

TABLE 9

| | Mental Component Score | |
|---|---|---|
| Day | Mean ± SD (mg/dl) | % Reduction |
| 15 | 25.63 | 52.52% |
| 30 | 39.67 | |
| 90 | 53.98 | |

Example 4: Study of Efficacy of Test Drug in the Management of Insulin Dependent Diabetes Mellitus Introduction:

Type I diabetes is also known as insulin-dependent diabetes mellitus (IDDM) caused mainly due to less production of insulin. Type II diabetes, on the other hand, also known as non-insulin-dependent diabetes mellitus (NIDDM) is caused mainly due to the inability of body cells to respond to the insulin produced.

Test drug has shown highly encouraging results in the management of Type II (NIDDM) diabetes mellitus. In experimental study test drug was found to regenerate 1 cells of islets of pancreas that secrete insulin. Hence it was planned to try the test drug among the patients of IDDM with regular careful follow up.

Materials and Methods:

Adult patients (20 years to 60 years) under insulin therapy were selected for the study. Juvenile diabetes mellitus and patients with complications are excluded from the study.

Study was obtained Institutional Ethical Clearance. Patients were enrolled after taking written consents. All the clinical features, detailed history and investigative findings are recorded in the specially designed clinical proforma.

Dose: Initial dose was two tablets twice daily after food. When normoglycemic stage is attained with Fasting Blood Sugar Less than 110 mg/dl and Post Prandial Blood Sugar less than 140 mg/dl and HBA1C within 6.5, Insulin dose was gradually tapered and dose of test drug was increased to two tablets thrice daily.

Duration: Study was carried out for three months. It was a single blinded clinical study with pre and post-test design.

Total number of patients studied: 18

Maximum numbers of patients were of the age group between 41 and 50 years. Majority of the patients were male. Table 10 illustrates the age and sex wise distribution of the patients.

TABLE 10

| | Distribution of the patients-age and sex. | | |
|---|---|---|---|
| Age | Male | Female | Total |
| 21-30 years | 01 | 00 | 01 |
| 31-40 years | 02 | 01 | 03 |
| 41 to 50 years | 06 | 04 | 10 |
| 51 to 60 years | 02 | 02 | 04 |
| Grand total | 11 | 07 | 18 |

Majority of the patients were on Insulin since less than 5 years. Table 11 illustrates distribution according to the chronicity of the disease.

TABLE 11

| Distribution of the patients-chronicity of the disease | |
|---|---|
| Years | No. of patients |
| Less than 5 years | 11 |
| 6-10 years | 04 |
| 10-15 years | 02 |
| 15-20 years | 01 |
| Above 20 years | 00 |

All the patients were under Human Mixtard Insulin (70:30). Table 12 illustrates distribution of patients according to Insulin dose. Maximum numbers of patients were taking Insulin between 21 and 30 units.

TABLE 12

| Distribution of patients-Insulin unit/day. | |
|---|---|
| Units per day | No. of patients |
| Less than 10 | 02 |
| 11-20 | 02 |
| 21-30 | 10 |
| 31-40 | 03 |
| Above 40 units | 1 |

Results:

Table 13 illustrates the effect of Test drug on Fasting blood sugar.

TABLE 13

| | FBS data | |
|---|---|---|
| Day | Mean ± SD (mg/dl) | % Reduction |
| 1 | 179.24 ± 41.39 | 36.78% |
| 15 | 162.63 ± 35.24 | |
| 30 | 143.78 ± 33.58 | |
| 90 | 113.31 ± 25.97 | |

Table 14 illustrates the effect of Test drug on Post Prandial blood sugar.

TABLE 14

| | PPBS data | |
|---|---|---|
| Day | Mean ± SD (mg/dl) | % Reduction |
| 1 | 208.24 ± 41.39 | 35.98% |
| 15 | 187.63 ± 35.24 | |
| 30 | 169.78 ± 33.58 | |
| 90 | 133.31 ± 25.97 | |

Table 15 illustrates the effect of Test drug on HbA1c level.

TABLE 15

| HbA1c data | | |
| --- | --- | --- |
| Day | Mean ± SD (mg/dl) | % Reduction |
| 1 | 8.95 ± 1.67 | 30.61% |
| 90 | 6.21 ± 0.98 | |

Table 16 illustrates the effect of test drug on Insulin dose.

TABLE 16

| Reduction in Insulin dose | | |
| --- | --- | --- |
| Before treatment | After treatment | % Reduction |
| 27 ± 1.12 | 18 ± 1.67 | 33 |

Observation:

The study is highly encouraging as it was observed that the need of insulin among the patients after the treatment is reduced. All the patients under test were on both oral hypoglycemic drugs and Insulin. Two patients taking Insulin less than 10 units per day could completely stop insulin and remain on oral hypoglycemic agents. The findings suggest that Insulin secretion is improved in the patients. Experimental study has also shown that test drug helps to regenerate degranulated β cells in islets of pancreas.

Herbs like Punarnava (*Boerhavia diffusa*), Kumari (Aloe vera) present in the formulation are known to have insulinomimetic activity. Ingredients like Aloe vera and *Mucuna pruriens* increase insulin secretion. Ingredients like *Salacia* act as anti-oxidants, improves body's sensitivity to insulin and supress glucose absorption. Phyto constituents like alkaloids inhibit alpha-glucosidase and decrease glucose transport through the intestinal epithelium. Imidazoline compounds stimulate insulin secretion in a glucose-dependent manner. Polysaccharides increase the level of serum insulin, reduce the blood glucose level and enhance tolerance to glucose. Flavonoids suppress the glucose level, reduce plasma cholesterol and triglycerides significantly and increase hepatic glucokinase activity probably by enhancing the insulin release from pancreatic islets.

CONCLUSION

Even though the sample size is small initial observations clearly indicate that test drug can be effectively used among the diabetes patients who are already on insulin therapy. Dose of insulin was reduced and glycemic control was improved.

The treatment regimen employing the embodiments of the Disclosed formulation and the dosages may vary depending on the patient. The embodiments disclosed herein were evaluated as per international OECD guidelines (423, 407, 408 and 452) and was found to be safe and non-toxic. The LD50 value of test drug was found to be greater than 5000 mg/kg body weight and classified as Category-5 or unclassified based on Globally Harmonised Classification System (GHS) for Chemical Substances and Mixtures.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

I claim:

1. A formulation for treatment and management of Diabetes, comprising:

*Salacia chinensis* in an amount in the range of 4 to 8 wt %,
*Gymnema sylvestre* in an amount in the range of 4 to 8 wt %,
*Emblica officinalis* in an amount in the range of 2 to 6 wt %,
*Eugenia jambolana* in an amount in the range of 4 to 8 wt %,
*Curcuma longa* in an amount in the range of 3 to 7 wt %,
*Commiphora mukul* (Guggulu) in an amount in the range of 3 to 7 wt %,
*Tinospora cordifolia* in an amount in the range of 3 to 7 wt %,
*Withania somnifera* in an amount in the range of 1 to 4 wt %,
*Terminalia chebula* in an amount in the range of 1 to 4 wt %,
*Terminalia bellerica* in an amount in the range of 1 to 4 wt %,
*Andrographis paniculata* in an amount in the range of 1 to 4 wt %,
*Boerhavia diffusa* in an amount in the range of 1 to 4 wt %,
*Azadirachta indica* in an amount in the range of 1 to 4 wt %,
*Aristolochia indica* in an amount in the range of 1 to 4 wt %,
*Aegle marmelos* in an amount in the range of 1 to 4 wt %,
*Cyperus rotundus* in an amount in the range of 1 to 4 wt %,
*Hemidesmus indicus* in an amount in the range of 1 to 4 wt %,
*Trichosanthes dioica* in an amount in the range of 1 to 4 wt %,
*Santalum alba* in an amount in the range of 1 to 4 wt %,
*Terminalia arjuna* in an amount in the range of 1 to 4 wt %,
*Woodfordia fruticosa* in an amount in the range of 1 to 4 wt %,
*Glycyrrhiza glabra* in an amount in the range of 1 to 4 wt %,
*Mucuna pruriens* in an amount in the range of 1 to 4 wt %,
*Myrica nagi* in an amount in the range of 1 to 4 wt %,
*Plumbago rosea* in an amount in the range of 1 to 4 t %,
*Inula racemosa* in an amount in the range of 1 to 4 wt %,
*Zingiber officinalis* in an amount in the range of 1 to 4 wt %,
*Piper longum* in an amount in the range of 1 to 4 wt %,
*Piper nigrum* in an amount in the range of 1 to 4 wt %, or extracts thereof;
Shilajit in an amount in the range of 2 to 6 wt %;
Abhraka Bhasma in an amount of ≤2 wt %;
Vanga Bhasma in an amount of ≤1 wt %;

Yashada Bhasma in an amount of ≤1 wt %;
Pravala Bhasma in an amount of ≤2 wt %;
Loha Bhasma in an amount of ≤2 wt %;
Swarna Makshika Bhasma in an amount of ≤2 wt %; and
Gum acacia in an amount in the range of 8 to 10 wt %, of the total composition.

2. The formulation as claimed in claim 1, further comprising gum acacia.

3. The formulation as claimed in claim 1, further comprising at least one additive selected from the group consisting of a flavor, a colorant, a preservative, and a pH adjuster.

4. The formulation as claimed in claim 1, wherein said formulation is administered in a form selected from the group consisting of powder, emulsion, tablets, capsules, troches and pills.

5. The formulation as claimed in claim 1, wherein said formulation is in the form of a tablet.

6. The formulation as claimed in claim 5, wherein said tablet is in the form of 500 mg tablet.

7. A method for the treatment of a condition selected from a group consisting of diabetes, hyperglycemia, low glucose tolerance, hyperinsulinemia and related complications, comprising administering to a patient in need thereof an effective amount of the formulation as claimed in claim 1.

8. A process for the preparation of formulation as claimed in claim 1, comprising:
 levigating bhasmas, Guggulu and shilajit;
 adding finely powdered herbs; and
 adding grinding decoction while continuing grinding to obtain a ground mass.

9. The process for the preparation of formulation as claimed in claim 8, wherein said bhasmas include Abhraka Bhasma, Vanga Bhasma, Yashada Bhasma, Pravala Bhasma, Loha Bhasma and Swarna Makshika Bhasma.

10. The process for the preparation of formulation as claimed in claim 8, wherein said finely powdered herbs comprises of finely powdered form of at least one herb selected from a group consisting of dried root of *Salacia chinensis*, dried root of *Withania somnifera*, dried root of *Boerhavia diffusa*, dried root of *Aristolochia indica*, dried root of *Aegle marmelos*, dried root of *Cyperus rotundus*, dried root of *Hemidesmus indicus*, dried root of *Glycyrrhiza glabra*, dried root of *Inula racemosa*, dried root of *Plumbago rosea*, dried fruits of *Terminalia chebula*, dried fruits of *Terminalia bellerica*, dried fruits of *Emblica officinalis*, dried fruits of *Piper longum* and dried fruits of *Piper nigrum*, dried bark of *Azhadirachta indica*, dried bark of *Myrica nagi*, dried bark of *Terminalia arjuna*, dried plant of *Andrographis paniculata*, dried plant of *Trichosanthes dioica*, dried leaves of *Gymnema sylvestre*, dried heartwood of *Santalum alba*, dried flowers of *Woodfordia fruticosa*, dried seeds of *Mucuna pruriens*, dried seeds of *Eugenia jambolana*, dried rhizome of *Curcuma longa*, dried rhizome of *Zingiber officinalis* and dried stem of *Tinospora cordifolia*.

11. The method of treating diabetes and associated complications as claimed in claim 7, wherein said therapeutically effective amount is 500 to 1000 mg administered one to three times a day.

12. The method as claimed in claim 7 wherein said formulation is administered along with administration of at least one other medication prescribed for treatment of Diabetes and associated complications.

\* \* \* \* \*